United States Patent
Cooney et al.

(10) Patent No.: US 7,586,020 B2
(45) Date of Patent: Sep. 8, 2009

(54) METHODS FOR DETERMINING EFFECTS OF MATERNAL TREATMENTS ON OFFSPRING

(76) Inventors: Craig Anthony Cooney, 12413 Timber Bend Dr., Little Rock, AR (US) 72211; George Louis Wolff, 2802 Millbrook Rd., Little Rock, AR (US) 72227

( * ) Notice: Subject to any disclaimer, the term of this patent is extended or adjusted under 35 U.S.C. 154(b) by 0 days.

(21) Appl. No.: 10/402,704

(22) Filed: Mar. 29, 2003

(65) Prior Publication Data

US 2004/0033198 A1 Feb. 19, 2004

Related U.S. Application Data

(62) Division of application No. 09/330,771, filed on Jun. 11, 1999, now Pat. No. 6,541,680.

(60) Provisional application No. 60/089,053, filed on Jun. 12, 1998.

(51) Int. Cl.
*A01K 67/00* (2006.01)
*A61K 31/525* (2006.01)
*A61K 31/70* (2006.01)
*A01N 57/26* (2006.01)

(52) U.S. Cl. ............... 800/8; 424/9.1; 514/251; 514/52; 514/77

(58) Field of Classification Search ............... None
See application file for complete search history.

(56) References Cited

OTHER PUBLICATIONS

Crystal (1995) Science, 270: 404-410.*
Gura (1997) Science, 278: 1041-42.*
Morgan, et al (1999) Nature Genetics, 23: 314-18.*
Yen, et al. (2002) FASEB J., 8: 479-488.*
Hugh Morgan et al., Epigenetic inheritance at the *agouti locus* in the mouse. *Nature Genetics*. vol. 23, 1999, pp. 314-318.
Information Disclosure Statements of Applications 09/330,771.
Gura (1997) Science, 278: 1041-1042.
W.E. Heston and G. Vlahakis (1968) C3H-Avy-a high hepatoma and high mammary tumor strain of mice. J Natl Cancer Inst. Jun.; 40(6):1161-6.
George L. Wolff, Dean W. Roberts, et al. (1987) Tumorigenic responses to lindane in mice: potentiation by a dominant mutation. Carcinogenesis. Dec;8(12):1889-97.
G. Vlahakis, W.E. Heston and G.H. Smith (1970) Strain C3H-A-vy-fB mice: ninety percent incidence of mammary tumors transmitted by either parent. Science. Oct. 9;170(954):185-7.
George L. Wolff, et al. (1979) Manifestation of hyperplastic alveolar nodules and mammary tumors in "viable yellow" and non-yellow mice. J Natl Cancer Inst. Sep.;63(3):781-5.
George L. Wolff, et al. (1982) Accelerated appearance of chemically induced mammary carcinomas in obese yellow (Avy/A) etc. J Toxicol Environ Health. Jul.;10(1):131-42.
G. Vlahakis and W.E. Heston (1971) Spontaneous cholangiomas in strain C3H-AvyfB mice and in their hybrids. J Natl Cancer Inst. Mar. 1971;46(3):677-83.
M.L. Klebig, et al. (1995) Ectopic expression of the *agouti gene* in transgenic mice causes obesity, etc. Proc Natl Acad Sci. May 23;92(11):4728-32.
Rosalynn J. Miltenberger, et al. (1997) The role of the *agouti* gene in the yellow obese syndrome. J Nutr. Sep;127(9):1902S-1907S.

* cited by examiner

*Primary Examiner*—Robert M Kelly

(57) ABSTRACT

The present invention provides animal models and methods for the evaluation of maternal treatments that could improve or compromise the epigenetic state, the imprinting, or the DNA methylation and thus the health or disease propensity, of human or other mammalian offspring. In particular, the present invention provides animal models with naturally occurring epigenetic variation for the evaluation of treatments through effects on the epigenetically determined and imprinted characteristics of coat color, coat color pattern, DNA methylation, long terminal repeat (LTR) expression and LTR activity of offspring.

8 Claims, 7 Drawing Sheets
(6 of 7 Drawing Sheet(s) Filed in Color)

METHODS FOR DETERMINING EFFECTS OF MATERNAL TREATMENTS ON OFFSPRING

RELATED APPLICATION

This is a division of Ser. No. 09/330,771, filed 1999 Jun. 11, and issued as U.S. Pat. No. 6,541,680. This application claims the benefit of priority under 35 U.S.C. § 119(e) of Provisional Application No. 60/089,053, filed 1998 Jun. 12.

SEQUENCE LISTING

1. PCR primer AVYCC6 designed to span the IAP LTR
2. PCR primer AVYCC856 complementary to agaaggtatgt-gctaaactc and designed to span the IAP LTR
3. Mus musculus intracisternal A particle (IAP)

FIELD OF THE INVENTION

The invention relates generally to a dietary supplement that increases DNA methylation, methods for altering the phenotype of offspring using the supplement, and methods for inhibiting retroviral expression using the supplement. The invention also relates to an animal model for epigenetic regulation of phenotypic expression.

BACKGROUND OF THE INVENTION

The maternal reproductive tract, arguably, is the environment most critical to the developing mammalian embryo. Its metabolic and physiologic characteristics modulate the zygote's development through all embryonic stages until birth. Indeed, the conditions in the embryo's immediate milieu seem to determine many characteristics and susceptibilities of the adult organism.

Mammalian development is dependent on DNA methyltransferase (MTase) and its product 5-methylcytosine (5MC) to help establish, define, or stabilize the various cell types that constitute the developing embryo. In mammals, 5MC is a major epigenetic mechanism, with some 5MC patterns being inherited epigenetically. DNA MTase requires S-adenosylmethionine (SAM) and uses zinc as a cofactor.

Synthesis of the chief methyl donor SAM is dependent on dietary folates, vitamin $B_{12}$, methionine, choline, and betaine, which are also available as nutritional methyl supplements. In the human maternal diet, folic acid is important for the prevention of neural tube birth defects, where it may act via methyl metabolism although the mechanism is presently unknown. Little is known about how, or if, maternal dietary methyl supplements affect epigenetic regulation of the developing mammalian embryo or whether high levels of certain methyl supplements are toxic. Cooney proposed that dietary methyl supplements given to adults could affect gene expression and 5MC levels in adults and that the level of gene-specific 5MC in young mammals could affect their adult health and longevity (Cooney, C. A. 1993 Growth Dev. Aging 57, 261-273).

The mouse agouti alleles, $A^w$ and A, regulate the alternative production of black (eumelanin) and yellow (pheomelanin) pigment in individual hair follicles. Transcription of the gene occurs only in the skin during the short period when the yellow subapical band is formed at the beginning of each hair growth cycle. This cyclic expression results in the 'agouti' coat pattern.

Due to mutations in the regulatory region of the agouti locus, mice bearing the dominant 'viable yellow' ($A^{vy}$), 'IAPyellow' ($A^{iapy}$), or 'hypervariable yellow' ($A^{hvy}$) alleles synthesize much more pheomelanin than eumelanin. These mutations arose through spontaneous insertions of single intracisternal A particle (IAP) sequences in different regions of the agouti gene, all preceding the first coding exon. In these yellow mice, the gene is under control of the MAP promoter/enhancer and is therefore transcribed continuously in essentially all tissues. This results, not only in yellow hair but also in obesity, hyperinsulinemia, diabetes, increased somatic growth, and increased susceptibility to hyperplasia and tumorigenesis.

IAP's are retrovirus-like particles produced from the expression of a repetitive DNA element endogenous in mammalian genomes. The term is also used for the DNA i.e. the endogenous retrovirus-like DNA sequence (repetitive DNA element). IAP expression is controlled by DNA methylation (i.e 5MC). More specifically the long terminal repeat (LTR) of many retroviruses and retrovirus-like elements like the IAP are controlled by DNA methylation. DNA methylation prevents LTRs from activating and driving gene expression. Many LTRs and IAPs are constitutively active unless methylated. Expression of IAPs and other retrovirus and retrovirus-like elements results in a variety of health problems in mice, humans, and other mammals.

Mice of the non-agouti genotype, a/a, are black in coat color and no pheomelanin is synthesized, except in hair follicles in the ears and perineal area, due to insertions of non-IAP retroviral sequences in the intron preceding the first coding exon of the agouti gene. Because the a allele produces neither yellow nor pseudoagouti phenotypes, it is often used as the second allele in studies with the dominant yellow mutants.

Expression of $A^{vy}$, $A^{iapy}$, and $A^{hvy}$ can be down-regulated epigenetically. In yellow $A^{iapy}$/a and $A^{hvy}$/a mice, the proximal IAP long terminal repeat (i.e IAP LTR), containing promoters and enhancers, is hypomethylated, whereas in pseudoagouti $A^{iapy}$/a mice and their black $A^{hvy}$/a homologs, the LTR is methylated. Thus, in pseudoagouti mice the IAP promoter is inactive, allowing the normal agouti promoters to regulate transcription of the gene. The mouse genotypes $A^{vy}$/a and $A^{iapy}$/a are expressed in almost identical phenotypes. Since the agouti protein is continuously and ectopically expressed in both mutants, it is likely that in $A^{vy}$/a mice, a regulatory mechanism is operative similar to that reported for $A^{iapy}$ and $A^{hvy}$.

A continuous spectrum of variegated patterns of eumelanic mottling (EM), i.e., agouti, on a yellow background characterizes $A^{vy}$/a mice. Their phenotypes are defined by the degree of EM (see the list of phenotypes in Example 1). Thus, a 'clear yellow' mouse (all yellow) is at one extreme of the EM spectrum and the 'pseudoagouti' mouse (all agouti, FIG. 1) occupies the other extreme. The latter resembles the agouti (A/-) coat color phenotype, does not become obese, is normoinsulinemic, and is less susceptible to tumorigenesis.

Epigenetic changes are changes in the use or expression of genes and other DNA sequences by processes that do not change the DNA coding sequence itself. Epigenetic processes result in changes that are heritable from one cell generation to the next, thus providing for the maintenance of cellular differentiation. Epigenetic changes and processes can be heritable from one animal generation to the next. Epigenetic processes allow us to go from a single cell (fertilized egg or zygote) which is one cell type at conception, to a multicellular organism with many cell types as we develop as embryos and beyond. Epigenetic processes allow us to maintain our established cell types whether we are embryos, infants, children or adults. It is the breakdown of these epigenetic processes that contribute to the development of cancer as well as to aging and likely a number of other diseases. Most of these same epigenetic processes occur in all plants and animals studied. In particular fish, birds, mammals, plants, reptiles, amphibia and some fungi use DNA methylation as an epigenetic DNA and gene control mechanism. Importantly all mammals studied appear to use the same set of epigenetic mechanisms.

All mammals studied, especially all placental mammals, including humans and domesticated mammals, use basically the same epigenetic control mechanisms including DNA methylation, methylated DNA binding proteins, differential DNA replication timing in the cell cycle, histone acetylation, and differential chromatin condensation, to name a few common features. All mammals studied, especially all placental mammals, including humans and domesticated mammals, use basically the same methyl metabolism, have basically the same dietary requirements for methyl metabolism (albeit met by various means), have DNA MTase enzymes which require S-adenosylmethionine and are inhibited by S-adenosylhomocysteine and use zinc as a cofactor, as well as having numerous other features in common. These common features make it reasonable to expect that effects on basic processes in all mammals, especially all placental mammals, including humans and domesticated mammals, would share common features. Thus it would be reasonable to expect that specific dietary supplements or specifically altered dietary balances would affect the epigenetics and/or phenotype of offspring in all mammals, especially all placental mammals, including humans and domesticated mammals.

Many of the mechanisms used to control gene, repetitive sequence, repetitive DNA element, retrovirus, transposon and intragenomic parasite expression are common to a very broad range of organisms. For example birds, reptiles, fish, other vertebrates, some fungi, and most plants studied use DNA methylation as a gene, repetitive sequence, repetitive DNA element, retrovirus, transposon and intragenomic parasite control mechanism. Likewise these and other eukaryotes have in common with mammals certain other epigenetic and gene, repetitive sequence, repetitive DNA element, retrovirus, transposon and intragenomic parasite control mechanisms. Several determinants of epigenetic inheritance are outlined in Example 6.

Morphological changes are not necessarily epigenetic in nature or in source. Therefore a change such as described by Meck et al. 1988 (Dev. Psychobiol. 21, 339-353) where maternal choline supplementation affects the memory of offspring is not known to be epigenetic, not known to involve epigenetic mechanisms and no specific gene or even DNA is known to be involved.

In $A^{vy}/a$ mice, there is partial maternal epigenetic inheritance of phenotype. In general, maternal epigenetic inheritance occurs when the epigenetic phenotype and/or allelic expression of the mother is a determinant of the epigenetic phenotype and/or allelic expression of the offspring. For $A^{vy}/a$ dams, the proportion of pseudoagouti offspring depends on the mother's agouti locus epigenetic phenotype.

In both $A^{vy}/a$ and $A^{iapy}/a$ mice, the proportions of zygotes differentiating into pseudoagouti phenotype offspring are determined by the gender of the parent contributing the mutant allele, as well as by the dam's strain genome. These gender and strain effects demonstrate, respectively, genomic imprinting and strain-specific modification of the $A^{vy}$ and $A^{iapy}$ alleles.

Genomic imprinting occurs when the level of allelic expression in offspring depends on the gender of the parent contributing the allele. Imprinting is a parental gender effect on gene expression in offspring but is neither the inheritance of a parent's epigenetic somatic characteristics nor the inheritance of a parent's somatic allelic imprint (although these may happen to coincide between parent and offspring).

SUMMARY OF THE INVENTION

One aspect of the invention provides a maternal nutritional supplement which can positively affect health and longevity of the offspring comprising at least two of the following: about 5-15 g/kg diet/day of Choline, about 5-15 g/kg diet/day of Betaine, about 5-15 mg/kg diet/day of Folic acid, about 0.5-1.5 mg/kg diet/day of Vitamin $B_{12}$, about 0 to 7.5 g/kg diet/day of L-Methionine, and 0 to 150 mg/kg diet/day of Zinc. The concentrations are preferably about 10-15 g/kg diet/day of Choline, about 10-15 g/kg diet/day of Betaine, about 10-15 mg/kg diet/day of Folic acid, about 1.0-1.5 mg/kg diet/day of Vitamin $B_{12}$, about 5 to 7.5 g/kg diet/day of L-Methionine, and 100 to 150 mg/kg diet/day of Zinc. The concentrations are even more preferably about 15 g/kg diet/day of Choline, about 15 g/kg diet/day of Betaine, about 15 mg/kg diet/day of Folic acid, about 1.5 mg/kg diet/day of Vitamin $B_{12}$, about 7.5 g/kg diet/day of L-Methionine, and 150 mg/kg diet/day of Zinc.

The expression "kg/diet/day" or "per kg diet per day" means daily or equivalent, regular, supplementation at a particular level per kilogram of food or diet that would normally be eaten. Supplementation may be taken with, at the same time as, or at a different time than, the food or diet. Supplementation could be taken on a day, or on days, when food isn't eaten or when food or diet is restricted but where the supplementation level is approximately equivalent to that which would be taken in a day if food or diet were consumed at a "normal" ad libitum rate and if food or diet contained the supplement at the particular level per kilogram of food or diet.

A further aspect of the invention provides a method for screening for substances that affect epigenetic changes in offspring. The method uses a model consisting of a recessive non-agouti (a/a) female mouse which has been or will be mated with a heterozygous viable yellow male mouse ($A^{vy}/a$). The substance or treatment is administered to the unborn offspring and the phenotype of the offspring is measured after birth. In one embodiment the substance can be administered by administering it to the mother before and/or during pregnancy. In another embodiment it can be administered in vivo. In another embodiment it can be administered in vitro to a fertilized egg, zygote, embryo or fetus. In one embodiment the measurement can be by visual examination of the coat color pattern. In another embodiment the measurement can be by quantitation of 5-methylcytosine in a cell, tissue or body fluid. In a further embodiment the measurement can be by quantitation of DNA methylation of the IAP LTR. An additional way to express use of these treatments is to prepare or condition the female and her oocytes in vivo or in vitro in order to affect the developmental processes following fertilization.

A further aspect of the invention is a method for screening for substances that affect the expression of parasitic DNA sequences. The method uses a model consisting of a pregnant recessive non-agouti (a/a) female mouse which has been mated with a heterozygous viable yellow male mouse ($A^{vy}/a$). The substance or treatment is administered to the unborn offspring and the phenotype of the offspring is measured after birth. In one embodiment the substance can be administered by administering it to the mother before and/or during pregnancy. In another embodiment it can be administered in vivo. In another embodiment it can be administered in vitro to a fertilized egg, zygote, embryo, or fetus. In one embodiment the measurement can be by visual examination of the coat color pattern. In another embodiment the measurement can be by quantitation of 5-methylcytosine in a cell, tissue or body fluid. In a further embodiment the measurement can be by quantitation of DNA methylation of the IAP LTR. In a further embodiment the parasitic DNA sequences are those for which expression is regulated by DNA methylation.

A further embodiment of the invention is a method for changing the epigenetically determined phenotype and inhibiting parasitic DNA sequences by administering a pharmaceutical composition comprising one or more of the following: Choline, Betaine, Folic acid, Vitamin $B_{12}$, L-Methionine, and Zinc, wherein the amount administered is; about 5-15 g/kg diet/day of Choline, about 5-15 g/kg diet/day of Betaine, about 5-15 mg/kg diet/day of Folic acid, about 0.5-1.5 mg/kg diet/day of Vitamin $B_{12}$, about 0 to 7.5 g/kg diet/day of L-Methionine, and about 0 to 150 mg/kg diet/day of Zinc to an offspring before birth. In one embodiment the substance can be administered by administering it to the mother before and/or during pregnancy. In another embodiment it can be administered in vivo. In another embodiment it can be administered in vitro to a fertilized egg, zygote, embryo or fetus. An additional way to express use of these treatments is to prepare or condition the female and her oocytes in vivo or in vitro in order to affect the developmental processes following fertilization.

Yet another embodiment of the invention is a method for inhibiting expression of an IAP sequence in an unborn offspring by administering a pharmaceutical composition comprising one or more of the following: Choline, Betaine, Folic acid, Vitamin $B_{12}$, L-Methionine, and Zinc, wherein the amount administered is; about 5-15 g/kg diet/day of Choline, about 5-15 g/kg diet/day of Betaine, about 5-15 mg/kg diet/day of Folic acid, about 0.5-1.5 mg/kg diet/day of Vitamin $B_{12}$, about 0 to 7.5 g/kg diet/day of L-Methionine, and about 0 to 150 mg/kg diet/day of Zinc to an offspring before birth. In one embodiment the substance can be administered by administering it to the mother before and/or during pregnancy. In another embodiment it can be administered in vivo. In another embodiment it can be administered in vitro to a fertilized egg, zygote, embryo or fetus. An additional way to express use of these treatments is to prepare or condition the female and her oocytes in vivo or in vitro in order to affect the developmental processes following fertilization.

Still another embodiment of the invention is a method for reducing susceptibility to tumor-formation, and improving the health and longevity of an unborn offspring by administering a pharmaceutical composition comprising one or more of the following: Choline, Betaine, Folic acid, Vitamin $B_{12}$, L-Methionine, and Zinc, wherein the amount administered is; about 5-15 g/kg diet/day of Choline, about 5-15 g/kg diet/day of Betaine, about 5-15 mg/kg diet/day of Folic acid, about 0.5-1.5 mg/kg diet/day of Vitamin $B_{12}$, about 0 to 7.5 g/kg diet/day of L-Methionine, and about 0 to 150 mg/kg diet/day of Zinc to an offspring before birth. In one embodiment the substance can be administered by administering it to the mother before and/or during pregnancy. In another embodiment it can be administered in vivo. In another embodiment it can be administered in vitro to a fertilized egg, zygote, embryo, or fetus. An additional way to express use of these treatments is to prepare or condition the female and her oocytes in vivo or in vitro in order to affect the developmental processes following fertilization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
FIG. 1a. Adult strain VY mice showing some phenotypes resulting from agouti alleles. A black mouse (upper right) with a/a genotype and no significant agouti expression. A pseudoagouti (PA) mouse (lower middle) with $A^{vy}$/a genotype and having a "normal" agouti coat pattern due to cyclic, regulated agouti gene expression. A slightly mottled yellow (SMY) mouse (left) with $A^{vy}$/a genotype and having ectopic expression and overexpression of the agouti gene.
Figure 1B:
FIG. 1b. Strain VY mice at about eight days of age showing a black mouse (right) with a/a genotype and no significant agouti expression and a pseudoagouti (PA) mouse (left) with $A^{vy}$/a genotype and having a "normal" agouti coat pattern due to cyclic, regulated agouti gene expression.
Figure 1C:
FIG. 1c. Adult strain VY $A^{vy}$/a mice showing all epigenetically determined phenotypes except for 'almost pseudoagouti'. Mice clockwise from the right (at ~3 o'clock): a clear yellow (CY), two slightly mottled (SMY), a heavily mottled (HMY) and a mottled mouse (MY). A pseudoagouti (PA) mouse is in the center. All of these mice are genetically identical. All of these mouse coat patterns are due to the degree of agouti gene expression from the $A^{vy}$ allele.
Figure 1D:
FIG. 1d. Adult strain VY $A^{vy}$/a mice showing a top view. Starting from the right, a clear yellow (CY), a slightly mottled (SMY), a mottled (MY) and a heavily mottled (HMY) mouse. All of these mice are genetically identical. All of these mouse coat patterns are due to the degree of agouti gene expression from the $A^{vy}$ allele.

The present invention provides methods for altering the epigenetics and DNA methylation of mammalian offspring by treatments given their mothers before and during pregnancy. Further provided are methods for altering the epigenetics and DNA methylation of mammalian offspring by treatments given their mothers before and during pregnancy in animals in need of such a treatment. Also provided are novel pharmaceutical and nutritional compositions. Further provided are means to prevent disease in adult offspring and extend healthful longevity in offspring by treatments given their mothers before and during pregnancy. In this present invention two genetic strains of 'viable yellow' ($A^{vy}$/a) mice are used which differ in their adult propensity to disease. In each strain the 'yellow' epigenetic phenotypes of mice are larger, obese, hyperinsulinemic, more susceptible to cancer, and, on average, shorter lived than their non-yellow epigenetic phenotype siblings. 'Viable yellow' mice are epigenetic mosaics ranging from a yellow phenotype with maximum ectopic agouti overexpression, through a continuum of mottled agouti/yellow phenotypes with partial agouti overexpression, to a pseudoagouti phenotype with minimal ectopic expression. Pseudoagouti $A^{vy}$/a mice are lean, healthy, and longer lived than their yellow siblings. Here we report that feeding pregnant black a/a dams methyl-supplemented diets alters epigenetic regulation of agouti expression in their offspring, as indicated by increased agouti mottling in the direction of the pseudoagouti phenotype. We also present confirmatory evidence that epigenetic phenotypes are maternally heritable. We also show that $A^{vy}$/a mice with minimal ectopic expression of agouti have high levels of DNA methylation in the IAP LTR in the $A^{vy}$ allele. In contrast, we show that $A^{vy}$/a mice with maximal ectopic expression of agouti have low levels of DNA methylation in the IAP LTR in the $A^{vy}$ allele. IAP LTRs and closely related endogenous retroviral sequences are common in mammlian genomes and their activity is supressed by DNA methylation. Agouti gene expression from the $A^{vy}$ allele is responsible for the coat color pattern, health and longevity of $A^{vy}$/a mice. Thus $A^{vy}$ expression, already known to be modulated by imprinting, strain-specific modification, and maternal epigenetic inheritance, is also modulated by maternal diet. Maternal diet acts, at least in part, by affecting DNA methylation. These observations show that maternal dietary supplementation can positively affect health and longevity of the offspring. Therefore, this experimental system should be useful for identifying maternal factors that modulate epigenetic mechanisms, especially DNA methylation, in developing embryos.

The present invention was made, at least in part, through use of an animal model which takes advantage of methylation-dependent expression patterns of the agouti gene which determines coat color/pattern in mice. We show herein that our system is powerful, useful, novel and unique because changes in coat color of offspring changeable by the maternal environment (particularly diet) are readily apparent using the unaided senses (in particular vision). The epigenetic developmental history, the risk of certain adult onset diseases and the lifespan ranges of these mice are "written on their backs". Coats of these mice are readily apparent gauges of epigenetic events that have occurred in the development of these mice. These epigenetic events are analogous and similar, if not identical, in type, range and magnitude to epigenetic events that occur in the development of other mammals. Other mammals either lack such readily apparent gauges of epigenetic events or else the know-how to utilize or read these gauges is lacking. Other future systems might follow our invention and use other epigenetically determined features of offspring and/or phenotypic changes in offspring affected by maternal environment that are readily apparent to the unaided senses. These readily apparent changes could include, but are not limited to, hair length, type or color, body shape or form, altered sounds made by the offspring, distinctive smells and/or tastes produced by the offspring, a distinctive behavior, or a distinctive feel of the offspring. This could include any readily apparent or readily discerned change in the nature of the offspring.

We additionally show that a maternal nutritional supplement can change an epigenetically regulated process in mammalian offspring and that the changes can be reasonably expected to produce multigenerational effects. In addition, the treatment which increased DNA methylation did not adversely affect the mother or offspring.

We further show that the maternal nutritional supplement can change expression or activity of a retroviral, retrovirus-like, parasitic DNA sequence in the mammalian offspring.

The agouti animal model mice, in addition to the differences in coat color also show some other phenotypic differences. The mice having the yellow coat color are obese and susceptible to tumor formation, while their agouti (i.e. brown-colored) isogenic siblings are leaner, healthier, and live longer. It is known in related systems, and we show herein, that suppression of the yellow phenotype is correlated with increased methylation in or near the long terminal repeat (LTR) of an intracisternal A particle (IAP) sequence inserted in the 5' end of the agouti gene. This methylation of the IAP sequence occurs during embryonic development, and the resulting coat color remains stable through adulthood. We have found that feeding pregnant mice a diet supplemented with high levels of methylation-enhancing agents increases the number of offspring having the agouti pattern (brown-colored) phenotype. The supplemented diet causes differentiation toward the pseudoagouti phenotype of $A^{vy}$/a embryos. Thus, epigenetic regulation of the $A^{vy}$ allele is modulated not only by imprinting, strain-specific modifier effects, and maternal epigenetic inheritance, but also by the maternal diet. The present invention has three general components: (1) a dietary supplement; (2) methods for altering the phenotype of offspring, and methods for inhibiting retroviral expression and increasing DNA methylation; and (3) an animal model for epigenetic regulation of phenotypic expression.

Although other materials and methods similar or equivalent to those described herein can be used in the practice or testing of the present invention, the preferred methods and materials are now described.

In the following examples, data from two types of studies are presented. In dietary studies (Example 4), the effects on offspring of maternal diet during pregnancy were determined. In maternal epigenetic inheritance and imprinting studies, (Example 5), the effects on offspring of maternal epigenetic phenotype and of the gender of the parent contributing the $A^{vy}$ allele were determined in animals fed only the control diet. Examples 1-3 explain the materials and methods used in the two studies.

EXAMPLE 1

Mice Genotypes and Phenotypes Used in Both Studies

Inbred mouse strains YS/WffC3Hf/Nctr-$A^{vy}$ (i.e. YS) and VY/WffC3Hf/Nctr-$A^{vy}$ (i.e. VY) were used for dietary studies at $F_{116}$-$F_{120}$ of YS and $F_{107}$-$F_{111}$ of VY and for maternal epigenetic inheritance studies. The designations $F_{116}$-$F_{120}$ of YS and $F_{107}$-$F_{111}$ of VY refer to the number of inbred generations of the YS and VY strains. These designations indicate a high degree of genetic homogeneity within each strain. In dietary studies, black a/a females were date-mated at 6-8 wk of age to the same strain of mottled yellow or pseudoagouti $A^{vy}$/a males to produce litters of black a/a and various phenotypes of $A^{vy}$/a mice. The litters were phenotyped at 8 and 21 days of age. The spectrum of mottling (i.e. EM) necessitated the definition of six phenotypic classes for the purpose of grading offspring in dietary studies.

Mouse strains used in the diet studies were inbred and genetically homogeneous (save for the intentional heterozygosity at the $A^{vy}$ and a alleles of agouti). Note that either strains YS or VY can carry the $A^{vy}$ allele, as could other strains of mice if it were bred into them. Strain VY and strain YS are just names and do NOT relate to whether or not these strains necessarily carry the $A^{vy}$ allele. Note that there are strain VY and strain YS mice homozygous for the a allele of agouti i.e. a/a these are NOT carrying an $A^{vy}$ allele. Each strain used was inbred for over 100 generations. The exact number of inbred generations is not key to these results provided that the animals are inbred for enough generations to be considered genetically homogeneous (about 30 generations of inbreeding is enough). Inbred animals are not required to practice the invention. Inbred animals are used here to most clearly demonstrate utility. Two strains were used that differ in their genetic background and expression of agouti gene from the $A^{vy}$ allele and differ in their response to diet as well as their adult disease susceptibility. Note that the two strains can be visually distinguished by the recessive white spotting (s) of the YS strain as observable in animals of FIG. 1e and 1f. Because diet effects were seen in two different strains of mice it is very apparent that these effects should be applicable to many, if not all, strains of mice. Because mice are a good model for the responses of other mammals including humans and because mice and all mammals studied including humans use the same basic gene regulatory mechanisms, including DNA methylation, then it is reasonable that these effects should be applicable to other mammals including humans.

Mice of the non-agouti genotype a/a are black in coat color. On their backs, heads and most of the rest of their bodies they produce black pigment in their hair (but not yellow pigment). Black is the default color for nearly all of the coat because in a/a mice in nearly all of the coat and skin the agouti gene is not appreciably active, does not make agouti protein and does not cause production of yellow pigment.

Mice of the $A^{vy}$/a genotype produce a variety of phenotypes and coat color patterns. In $A^{vy}$/a mice the only appreciable expression of the agouti gene is from the $A^{vy}$ allele. The degree of expression from the agouti gene of the $A^{vy}$ allele can be determined simply from observing the coat color pattern of the animal.

Pseudoagouti phenotype mice have small amounts of agouti gene expression in their hair follicles over their entire coats. This agouti gene expression is enough to cause production of yellow pigment in their hair follicles alternately with the production of black pigment. This combined yellow and black pigment production leaves pseudoagouti animals with entirely agouti pattern coats. In lay terms, the agouti pattern gives a "brownish" or "brownish-grayish" coat color. This color arises from the combination of black and yellow banding on most individual hair shafts. (It is however technically incorrect to call the agouti or pseudoagouti mice "brown" or "brown-gray"). The exact appearance of this agouti coat color can vary with lighting, photography and imaging techniques but is, in any case, clearly distinct from the yellow coat color and the black coat color.

Clear yellow mice have a high level of agouti gene expression driven by the LAP LTR of the $A^{vy}$ allele. This high level of agouti expression is throughout the mouse (at least in several tissues studied) and produces a yellow coat as well as a number of adverse health effects. This high level of agouti expression and production of yellow pigment in the hair is to the exclusion of appreciable black pigment in the hair.

Generally most $A^{vy}$/a mice have a mottled or patchwork or striped coat color pattern that is a combination of yellow sections and agouti sections. Thus the degree of agouti gene expression is apparent from the pattern on their coats. These combination patterns give definition to most of the phenotypes namely, Slightly Mottled Yellow, Mottled Yellow, Heavily Mottled Yellow, Almost Pseudoagouti'.

The following list defines the six phenotypic classes of these $A^{vy}$/a mice as well as the one phenotypic class of a/a mice.

Clear Yellow—CY— All yellow coat (technically<2 mm$^2$ of agouti pattern on a 21 day old mouse). $A^{vy}$/a genotype.

Slightly Mottled Yellow —SMY— Majority yellow coat (no more than one-third or 0.33 of coat area is agouti). $A^{vy}$/a genotype.

Mottled Yellow—MY—About half yellow coat (> one-third or 0.33 but< two-thirds or 0.67 of coat area is agouti). $A^{vy}$/a genotype.

Heavily Mottled Yellow—HMY—Minority yellow coat (at least two-thirds or 0.67 of coat area is agouti). $A^{vy}$/a genotype.

Almost Pseudoagouti' —APA—Most of coat is solid agouti but a small portion (usually the lower right or left portion of the back) has faint yellow stripes. This Almost Pseudoagouti—APA—is a special phenotype thus far only seen in animals whose mothers were fed 3SZM diet during pregnancy. $A^{vy}$/a genotype.

Pseudoagouti—PA—All agouti coat, no yellow coat (technically<2 mm$^2$ of yellow coat on a 21 day old mouse). $A^{vy}$/a genotype.

Black—All black coat (No yellow, no agouti). Only a/a genotype.

Examples of all these mice are shown in FIGS. 1a-f.

EXAMPLE 2

Diets Used in Both Studies

Methyl-supplemented diets were designed to provide substantially increased amounts of cofactors and methyl donors for methyl metabolism and, in one diet, to provide additional zinc, a cofactor for the mouse and human DNA MTase. The methyl-supplemented diets, viz., standard methyl-supplemented diet (MS), HS (contains half of the supplement level in the MS diet), and 3SZM (contains 3x as much methyl supplement as MS diet plus zinc plus methionine), were prepared by fortifying the control 'methyl-sufficient'NIH-31 diet (Table 1).

TABLE 1

Composition of dietary methyl supplements*

| MS diet supplement | HS diet supplement | 3SZM diet supplement |
|---|---|---|
| 5 g Choline | 2.5 g Choline | 15 g Choline |
| 5 g Betaine | 2.5 g Betaine | 15 g Betaine |
| 5 mg Folic acid | 2.5 mg Folic acid | 15 mg Folic acid |
| 0.5 mg Vitamin $B_{12}$ | 0.25 mg Vitamin $B_{12}$ | 1.5 mg Vitamin $B_{12}$ |
|  |  | 7.5 g L-methionine |
|  |  | 150 mg Zinc |

*The above are added to NIH-31 diet to give 1000 g of the respective final diet. The final total amounts in 3SZM represent, in terms of the NIH-31 levels, ~9 times choline, ~9 times folic acid, ~60 times vitamin $B_{12}$, ~3.1 times methionine, and ~4.7 times zinc. Betaine not determined in NIH-31. Choline is from choline chloride, betaine is anhydrous, zinc is from $ZnSO_4 \cdot 7H_2O$. All components were obtained from Harlan Teklad (Madison, Wis.), except betaine which was from Finnsugar Bioproducts (Schaumburg, Ill.), and zinc, which was from Fluka (Milwaukee, Wis.).

These supplements contain folic acid, vitamin $B_{12}$, betaine, and choline in the same proportions but in different absolute amounts. The relative level of components in HS, MS, and 3SZM supplements is 0.5, 1.0, and 3.0, respectively. 3SZM supplement also contains methionine and zinc (in addition to threefold the MS level of folic acid, vitamin $B_{12}$, betaine, and choline). The absolute amounts of all components in the HS, MS, and 3SZM supplements are given in Table 1. Although there are many ways to supplement animals and their diets a best way to produce 3SZM diet follows. For 20 kg of 3SZM diet mix:

19.13 kg NIH-31 grind (i.e. ground NIH-31 diet)
    300 g Betaine (anhydrous)
    405 g Choline chloride (contains 300 g choline)
    300 mg Folic acid
    30 mg Vitamin $B_{12}$
    150 g L-Methionine
    13.3 g Zinc sulfate.7H20 (contains 3 g zinc)
    20 kg Total To mix:

Have 19.13 kg of NIH-31 grind weighed in "milk can" or other large stainless steel or plastic container.
Start ~10 kg of this mixing (conventional feed mixer).
Add betaine to this slowly (over at least 1 minute).
Add choline chloride to ~500 g NIH-31 grind (from weighed grind) in two ziplock bags and agitate and crush lumps with a flat or blunt object. Agitate these in the bags to homogeneity and then add this to the mixer slowly (at least 2 minutes).
Add folic acid to ~50 g NIH-31 grind (from weighed grind) in a ziplock bag or tube and shake to homogeneity and then add this to the mixer slowly (at least 1 minute).
Add vitamin $B_{12}$ to ~200 ml of water in a new spray bottle. Swirl until dissolved. Spray onto diet while mixing. Add ~100 ml more water, shake in spray bottle and spray this on diet while mixing.
Add L-methionine to diet while mixing.
Add zinc sulfate to ~200 ml of water in the spray bottle just used for vitamin $B_{12}$ (or a new spray bottle). Swirl until dissolved. Spray onto diet while mixing. Add ~100 ml more water, swirl in spray bottle and spray this on diet while mixing.
Add remaining weighed NIH-31 grind from milk can. Mix diet for an additional 20 minutes.

Notes for diets and mice:

Water used is double glass distilled water. Diet is made under NEAR sterile, clean conditions. New disposable face masks, hair & boot covers, overalls and gloves are used. Diets are pelleted and fed to mice as pellets. Pelleted diets are checked for significant levels of microbiological contamination as standard for conventional rodent diets. All of the supplemented nutrients are in a normal NIH-31 diet just at lower levels. (Although betaine is not measured in NIH-31 it is a normal part of animal and plant metabolism and thus will appear in the natural product diet NIH-31). This diet is not autoclaved after supplementation although all nutrients supplemented in this diet are known to survive autoclaving.

Supplemented and control diets were simply provided ad libitum to the mice in pelleted form on the indentation for pelleted feed on a wire top of a polycarbonate cage. Food and water are changed once a week.

Dams were put on their particular diets at least two weeks before mating and were taken off their supplemented diets after giving birth; however, to avoid possible health problems in dams or pups from abrupt diet change after giving birth, the dams were given lower dose diets for 1 or 2 wk before being placed solely on NIH-31 diet again. Two different schedules were followed: #1) MS diet for 2 wk before first date mating and through pregnancy, HS diet for the first week after birth, NIH-31 diet thereafter; #2) 3SZM diet for 2 wk before first date mating and through pregnancy, MS diet for first week after birth, HS diet for second week after birth, NIH-31 diet thereafter. Males were given the NIH-31(control diet) only except that they shared diet with supplemented females when they were put in female's cages for mating.

EXAMPLE 3

Statistical Analyses for Both Studies

For statistical analysis of the dietary studies, data from animals representing those with a majority of yellow in their coats (clear yellow, slightly mottled, and one-half of the mottled animals) were combined and compared with combined data from animals with a relatively high degree of EM in their coats (pseudoagouti, almost 'pdeudoagouti', heavily mottled, and the other one-half of the mottled mice). The 'mottled' category included mice with intermediate degrees of EM that could not be designated as either 'slightly' or 'heavily' mottled. For the statistical analysis, one-half of these mottled mice were assigned to the 'high EM' category and the remaining one-half to the 'low or no EM' category.

To detect a trend in the ratio of high to low degrees of EM across dietary groups, Rao-Scott tests were conducted separately for the YS and VY strains. To determine whether the two strains differed in these ratios, a stratified analysis, using the Cochran-Mantel-Haenszel test, was performed, with each dietary group serving as a stratum.

Whether methylated diets influenced the number of pups born or weaned was determined by analyses conducted separately for each strain using the SAS procedure GLM for single factor analysis of variance. Dunnett's test was used to compare each diet group to its appropriate control.

To analyze maternal epigenetic inheritance and imprinting data, comparisons of the proportions of pseudoagouti mice among $A^{vy}/a$ offspring were made for each strain between dams of various phenotypes, using chi-square tests for differences in proportions.

In Examples 4 and 5 the two studies are explained.

EXAMPLE 4

Dietary Studies

Dams (of a/a genotype, black coat) of two inbred mouse strains (YS and VY) were fed methyl-supplemented diets for at least two weeks prior to and during pregnancy and the degrees of EM of their offsprings' coats were determined. Maternal dietary methyl supplementation increased EM of the offspring in both mouse strains (Table 2). In strain VY mice, the MS diet produced a strong effect on offspring phenotype, with the proportion of offspring with high EM increasing from 42.7% with control diet to 59.8% on MS diet (P<0.001). In these strain VY mice, the 3SZM diet had the additional effect of inducing a new phenotype, 'almost pseudoagouti' (see below).

TABLE 2

Proportions of high and low degrees of eumelanic mottling (EM) among $A^{vy}/a$ offspring from a/a dams of two inbred strains fed methyl-supplemented diets

| Strain and diet | High EM[a] % (N) | Low or no EM[b] % (N) |
|---|---|---|
| Strain VY | | |
| NIH-31 (control) | 42.6 (75) | 57.4 (101) |
| MS | 59.8 (98)[c] | 40.2 (66)[c] |
| 3SZM | 65.8 (52)[c] | 34.2 (27)[c] |
| Strain YS | | |
| NIH-31 (control) | 65.6 (99) | 34.4 (52) |
| MS | 66.3 (67) | 33.7 (34) |
| 3SZM | 78.4 (69)[d] | 21.6 (19)[d] |

[a]Pseudoagouti + almost pseudoagouti + heavily mottled + ½ of the mottled pups.
[b]Slightly mottled + clear yellow + ½ of the mottled pups.
[c]P < 0.001 for VY strain and MS diet compared to control NIH-31 diet, as well as for the trend, NIH-31 < MS < 3SZM.
[d]P < 0.05 for YS strain with 3SZM diet compared to MS or NIH-31 diet and for the trend NIH-31 < MS < 3SZM.

In strain YS mice, the MS diet produced no significant effect on offspring phenotype, whereas the 3SZM diet increased the proportion of offspring with high EM from 65.5% on control diet to 78.4% on MS diet (P<0.05). The 3SZM diet also induced the new 'almost pseudoagouti' phenotype in these mice.

The Rao-Scott test indicated statistically significant differences in means and trend in phenotypic classifications among the three diet groups for the VY strain (P<0.001) and between the 3SZM and other diet groups in the YS strain (P<0.05). Methyl supplementation increased the ratio of high to low EM in the predicted direction (Table 2).

Figure 1E:
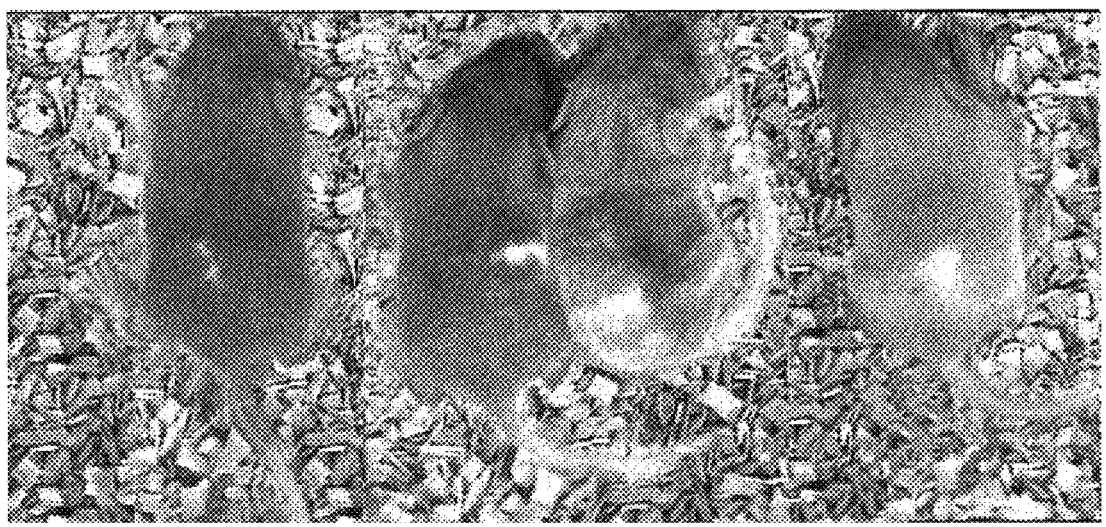
FIG. 1e. Strain YS $A^{vy}$/a mice at about eight days of age showing various epigenetically determined phenotypes. From left to right: pseudoagouti (PA), 'almost pseudoagouti' (APA), heavily mottled (HMY) and slightly mottled (SMY) mice. The 'almost pseudoagouti' (APA) and slightly mottled (SMY) phenotypes are found at opposite ends of a continuum of mottled mice in which each individual mouse has a unique pattern. Note the characteristic faint yellow stripes on the right rear quadrant of the 'almost pseudoagouti' (APA) mouse. The white spot on each mouse is due to recessive spotting (s) for which the YS strain is homozygous. The very light area on the rump of the heavily mottled mouse is a lighting artifact. All of these mice are genetically identical. All of these mouse coat patterns are due to the degree of agouti gene expression from the $A^{vy}$ allele.
Figure 1F:
FIG. 1f. Strain YS $A^{vy}$/a mice at about eight days of age showing two mice of 'almost pseudoagouti' (APA) phenotype. Note the characteristic faint yellow stripes on the right rear quadrant of each almost pseudoagouti' (APA) mouse. The white spot on each mouse is due to recessive spotting (s) for which the YS strain is homozygous.

A phenotype not previously observed by the grader (George Louis Wolff, $2^{nd}$ Inventor) in 30 years, designated 'almost pseudoagouti', was found only in litters from dams fed the 3SZM diet (FIGS. 1e and 1f). These mice have a few thin yellow lines or tiny spots, mainly in the rump area, on a pseudoagouti background and were found in ~13% (N=10) and ~20% (N=18) of VY and YS offspring, respectively. The APA phenotype usually have a few very thin yellow lines mainly in the lower right quadrant, OR lower left quadrant, of their backs on an otherwise pseudoagouti background. APA are distinguished from HMY in that HMY have more yellow and it is generally distributed over most of their coats. APA are distinguished from PA in that PA have virtually no yellow patches spots or lines in their coats. Examples of mice are given in FIGS. 1a-1f. Thus, the 3SZM diet greatly increased the proportion of mice that had 'almost' or entirely agouti coat color patterns.

The Cochran-Mantel-Haenszel test demonstrated a statistically significant difference between strains in the proportion of mice with high EM. This proportion was larger in all three dietary groups among YS mice than among VY mice (P<0.001) (Table 2).

Despite very high levels of supplementation (especially in the 3SZM diet, with over 4% w/w supplement), none of the diets exerted any detectable adverse effects on litter size, mortality between birth and weaning, health of the dams or that of the offspring until they were at least 6 wk old, or the ratio of a/a to $A^{vy}/a$ offspring.

EXAMPLE 5

Maternal Epigenetic Inheritance and Imprinting Studies

Analyses of breeding data from two time periods, separated by 20 years, revealed partial maternal epigenetic inheritance and imprinting with respect to epigenetic regulation of the $A^{vy}$ allele among animals on control diets (Table 3).

TABLE 3

Proportion of pseudoagouti mice among $A^{vy}/a$ offspring produced by yellow $A^{vy}/a$, pseudoagouti $A^{vy}/a$, and black a/a dams given control diet.

| | | Pseudoagouti $A^{vy}/a$ offspring | | | |
|---|---|---|---|---|---|
| DAM | SIRE | 1972-1977[a] | | 1991-1997 | |
| Geno(Pheno)type | Geno(Pheno)type | % | N | % | N |
| Strain VY[b] | | | | | |
| $A^{vy}/a$ (mottled yellow) | a/a | 1.0* | 17/1706 | 1.0** | 31/3015 |
| $A^{vy}/a$ (pseudoagouti) | a/a | 5.3* | 15/281 | 6.3** | 51/809 |
| a/a | $A^{vy}/a$ (mottled yellow) | 11.8 | 272/2296 | 10.2 | 237/2323 |
| a/a | $A^{vy}/a$ (pseudoagouti) | 10.1 | 60/593 | 9.3 | 62/669 |
| Strain YS[c] | | | | | |
| $A^{vy}/a$ (mottled yellow) | a/a | 0.3 | 2/607 | 0.2** | 5/2579 |
| $A^{vy}/a$ (pseudoagouti) | a/a | 1.2 | 4/329 | 2.3** | 5/216 |

TABLE 3-continued

Proportion of pseudoagouti mice among $A^{vy}/a$ offspring produced by yellow $A^{vy}/a$, pseudoagouti $A^{vy}/a$, and black a/a dams given control diet.

| DAM | SIRE | Pseudoagouti $A^{vy}/a$ offspring | | | |
|---|---|---|---|---|---|
| | | 1972-1977[a] | | 1991-1997 | |
| Geno(Pheno)type | Geno(Pheno)type | % | N | % | N |
| a/a | $A^{vy}/a$ (mottled yellow) | 16.8 | 49/292 | 7.0 | 181/2576 |
| a/a | $A^{vy}/a$ (pseudoagouti) | 16.9 | 72/427 | 8.4 | 19/225 |

[a]From Wolff, G.L. (1978) Genetics 88, 529-539 with permission.
[b]VY/Wf-$A^{vy}$ 1972-78; VY/WffC3Hf/Nctr- $A^{vy}$ 1978-1997.
[c]YS/ChWf- $A^{vy}$ 1972-78; YS/ChWffC3Hf/Nctr- $A^{vy}$ 1978-1997.
*$P < 0.001$ compared to other mating combinations using the same strain and time period.
**$P < 0.0001$ compared to other mating combinations within the same strain and time period.

These maternal epigenetic inheritance and imprinting studies were only done with control diet (NIH-31) and only determined whether offspring were black, pseudoagouti, or "mottled" yellow where the terms "mottled yellow" and "clear/mottled yellow" refer collectively to the combined phenotypes of Clear Yellow, Slightly Mottled Yellow, Mottled Yellow, Heavily Mottled Yellow. There are no 'almost pseudoagouti' mice in these maternal epigenetic inheritance and imprinting studies. Maternal epigenetic inheritance may be due either to the direct inheritance of epigenetic factors affecting gene expression from dam to offspring or to recapitulation in the offspring of the dam's pattern of gene expression and epigenetic allele modification due to metabolism, hormonal balance, or other factors in her uterine microenvironment.

The degree of maternal epigenetic inheritance can be measured by comparing the percentage of pseudoagouti offspring from pseudoagouti dams with that from mottled dams. For example, if the proportion of pseudoagouti $A^{vy}/a$ offspring from pseudoagouti dams is $P_p$ and the proportion of pseudoagouti $A^{vy}/a$ offspring from mottled yellow dams is $P_m$, then the ratio $P_p/P_m$ gives a value E, which is a measure of the degree of maternal epigenetic inheritance (i.e., $P_p/P_m = E$). There is maternal inheritance of epigenetic phenotype when $E>1$. In strain VY, the percentage of pseudoagouti $A^{vy}/a$ offspring from pseudoagouti dams was 6.3% in 1991-1997, whereas the percentage of pseudoagouti $A^{vy}/a$ offspring from mottled dams was 1.0% (Table 3). Thus $P_p/P_m$ was 6.3/1.0; E=6.3 and there was maternal epigenetic inheritance (E>1; $P<0.0001$). Therefore, in this case, pseudoagouti dams produced about 6.3-fold the proportion of pseudoagouti offspring as did yellow dams.

Pairwise comparisons between yellow, pseudoagouti, and black dams of the proportions of pseudoagouti offspring were highly significant ($P<0.001$). For both strains, the proportions of pseudoagouti offspring varied for dams of different phenotypes as follows: black>pseudoagouti>yellow.

Genomic imprinting occurs in $A^{vy}/a$ mice and can be measured by comparing the percentage of pseudoagouti offspring when the $A^{vy}$ allele is paternally inherited with that when the $A^{vy}$ allele is maternally inherited. For example, if the proportion of pseudoagouti $A^{vy}/a$ offspring from sires is $P_s$ and the proportion of pseudoagouti $A^{vy}/a$ offspring from dams is $P_d$, then the ratio $P_s/P_d$ gives a value G, which is a measure of the degree of genomic imprinting (i.e., $P_s/P_d = G$). There is genomic imprinting when $G \neq 1$.

When comparing mottled yellow parents, the percentage in strain VY of pseudoagouti $A^{vy}/a$ offspring from mottled $A^{vy}/a$ sires (dam was black a/a) was 10.2% in 1991-1997, whereas the percentage of pseudoagouti $A^{vy}/a$ offspring from mottled $A^{vy}/a$ dams (sire was black a/a) was 1.0% (Table 3). Thus, $P_s/P_d$ is 10.2/1.0, $G_m \cong 10$, and there is genomic imprinting ($G_m \neq 1$; $P<0.0001$).

When comparing pseudoagouti parents, the percentage in strain VY of pseudoagouti $A^{vy}/a$ offspring from pseudoagouti sires (dams were black a/a) was 9.3% in 1991-1997, whereas the percentage of pseudoagouti $A^{vy}/a$ offspring from pseudoagouti dams (sires were black a/a) was 6.3% (Table 3). Thus, $P_s/P_d$ is 9.3/6.3, $G_p \cong 1.5$, and there is genomic imprinting ($G_p \neq 1$; $P<0.02$).

That the $A^{vy}$ allele is imprinted is indicated by the greater proportion of pseudoagouti offspring when the $A^{vy}$ allele is contributed by the sire than when contributed by the dam. The degree of genomic imprinting depends on epigenetic phenotype, i.e., whether the parental gender comparison is of pseudoagouti mice or mottled yellow mice. In strain VY (in 1991 to 1997), $G_m \neq G_p$ ($P<0.001$).

Similar calculations can be made using the remaining data in Table 3 from both strains and both time periods. Thus, there is maternal epigenetic inheritance of alterations in $A^{vy}$ expression and an epigenetic influence on the degree of imprinting at $A^{vy}$.

EXAMPLE 6

Analysis of Both Studies

As indicated by increased proportions of the more strongly mottled phenotypes, methyl-supplemented diets affect expression of $A^{vy}$. With the control diet, we confirm important previous observations about the effects of maternal epigenetic phenotype and parental gender on $A^{vy}$ expression in offspring: 1) the epigenetic phenotype of $A^{vy}$ is, in part, maternally heritable, i.e., a pseudoagouti dam is more likely than a yellow dam to produce pseudoagouti offspring; 2) the gene is partly imprinted, i.e., if $A^{vy}$ is derived from the sire, the epigenetic phenotype of the offspring is much more likely to be pseudoagouti than when the gene comes from the dam. The current data show that diet and/or metabolic effects modulate IAP LTR expression, and would be expected to modulate strain-specific modifiers, maternal epigenetic inheritance, and imprinting-all factors in the epigenetic regulation of transcription of $A^{vy}$.

IAPs are endogenous retrovirus-like transposons with about 1000 copies each, widely dispersed in the mouse genome. IAP expression is regulated by DNA methylation and IAP activation of nearby genes is regulated by methylation or other epigenetic factors.

Similar sequences, human IAPs (i.e. HIAPs) are found in the human genome and their expression is associated with a number of immunological diseases. IAP expression is associated with adverse effects in both mice and humans due to activation of neighboring genes or transcription of the IAP itself; epigenetic suppression of IAPs and other repetitive sequences broadly affects genome integrity, and thus health. In the cases where IAP expression adversely affects health, certain diets and supplements could be used to suppress IAP expression and in turn exert positive effects on health.

Since hair follicle cells develop clonally from single precursor cells, there may be an inverse correlation between the degree of eumelanic mottling and the developmental stage at which the $A^{vy}$ IAP LTRs in the affected cells were epigenetically down-regulated. For example, if the IAP LTR of a precursor cell is down-regulated by methylation, the whole clone will produce eumelanin, except for normal yellow band production. This results in a large agouti area. If the methylation occurs later during clone formation, the eumelanic areas will be smaller, their specific size depending on the stage of clone development at which the IAP LTR methylation took place. The few yellow lines and spots that characterize the 'almost pseudoagouti' phenotype may represent a small number of hair follicle cells in which; for unknown reasons, the IAP LTRs were demethylated relatively late in clone formation. Alternatively, they may represent small clones derived from progenitor cells in which the IAP LTRs were never methylated or otherwise epigenetically down-regulated.

Epigenetic regulation of $A^{vy}$ expression is initiated during gametogenesis and development. $A^{vy}$ expression is also partly inherited maternally, suggesting that either epigenetic information is retained during gametogenesis and development or, if once lost, is recapitulated during these processes. This maternal influence, as well as the capacity to recapitulate, is evident from the modulation of expression of the paternal $A^{vy}$ allele by the maternal genotype. Paternal phenotype (yellow or pseudoagouti) has little or no effect on offspring phenotype, whereas maternal genotype and phenotype exert major effects. We show here for the first time that the maternal influence on expression is influenced strongly by maternal diet, is partly independent of genotype, and appears to be dependent on reproductive tract microenvironment and maternal metabolism. Strains differ in their distribution of phenotypes but this distribution can also be changed using supplements. The two strains we use here differ in their distribution of phenotypes when they are breed on the control diet, yet supplements can alter this relationship. For example, using supplements we can bring the phenotype of one strain (VY) to be similar to the control diet phenotype of another strain (YS). Whereas using supplements with YS strain we can move the YS strain phenotypic distribution even farther from the control diet phenotype distribution of VY strain. By analogy with other sequences whose epigenetic regulation is modified by the maternal genotype, regulation of $A^{vy}$ is also modulated by strain-specific modifiers. Thus, it is expected that some strain-specific modifiers act via metabolism or at least are dependent on diet and metabolism for their effects.

Important factors affecting $A^{vy}$ penetrance in the offspring are $A^{vy}$ expression in the mother and the sex of the parent contributing the $A^{vy}$ allele. Depending on the former, there can be large differences in penetrance among the offspring. Suppression of $A^{vy}$ expression in the pseudoagouti dam is partly inherited by some of her offspring (Table 3). This demonstrates that a specific epigenetic alteration of gene expression, resulting in the pseudoagouti phenotype, can be passed through the maternal germline to produce the same specific alterations in the offspring. Epigenetic inheritance is not limited to a single gender, as Roemer et al. (1997 Curr. Biol. 7, 277-280) reported partial paternal inheritance of epigenetic phenotypes of specific genes produced by nuclear transplantation.

This is the first demonstration of an effect of dietary methyl supplements on gene imprinting and specific gene expression, and shows that diet influences mechanisms of epigenetic regulation, imprinting, and development. Assays of 5MC in the IAP promoter in mottled yellow and pseudoagouti $A^{vy}/a$ mice in Example 9 show that 5MC is a mechanism in these epigenetic effects of diet in $A^{vy}/a$ mice.

TABLE 4

Some determinants of epigenetic inheritance

| Specific class | General category | Possible mechanisms in addition to 5 MC (All use 5 MC as a mechanism) |
|---|---|---|
| Maternal epigenetic phenotype (gene specific)* Possible multigenerational effects | Epigenetic inheritance | Chromatin marks carried through to the next generation. Uterine metabolic or hormonal factors. leading to recapitulation of a specific pattern of gene expression in offspring. These mechanisms could be influenced by maternal environmental factors |
| Paternal epigenetic phenotype (gene specific) Established multigenrational effects | Epigenetic inheritance | Initiated by nuclear transplantation in early embryos. Altered cytoplasmic environment in very early development leads to 5 MC changes and possibly other chromatin marks. Once established, these marks are directly or indirectly carried through to the next generation. |
| Maternal genotype** | Strain-specific modifiers | Specific genes acting in trans to produce gene products that effect epigenetic silencing, e.g., could be genes for transcription factors, chromatin factors, metabolism or signaling pathways. |
| Gender of parent contributing a particular allele** | Genomic imprinting | Gender-specific marking of germline genomes during germ cell development. Genomic imprinting can be partial or complete. |
| Maternal methyl-supplemented diets* Possible multigenerational effects | Maternal nutrition | MS diet: SAM and SAH levels, membrane fluidity, intracellular signaling, early embryo growth rate. 3SZM diet: Same as for MS diet plus greater zinc saturation of DNA MTase or other zinc finger chromatin proteins. |
| LAP LTR expression** Possible multigenerational effects | Transposition, cis-activation | Gene-regulating DNA sequence that is a target for 5 MC or other epigenetic silencing mechanism. |
| Transgene inactivation Variety of multigenerational effects | Gene silencing | Provides a DNA sequence that is a target for silencing and becomes epigenetically modified, often by 5 MC. |
| Monoallelic expression | Gene dosage adjustment | Sequence copy number in diploid cells. Parts of counting mechanisms to regulate gene dossage such as in X inactivation, e.g., 5 MC, chromatin, and specific RNAs such as Xist. |

*Observed in $A^{vy}/-$ mice.
**Observed in both $A^{vy}/-$ and $A^{iapy}/-$ mice.

Others have shown neurodevelopmental or biochemical effects of choline supplementation. Meck et al. (1988 Dev. Psychobiol. 21, 339-353) demonstrated a lifelong improvement in the memory of rats whose mothers were given choline supplements during pregnancy. Several metabolic parameters in dam and embryo were changed by maternal choline supplementation; however, no specific gene effects were identified. Most other examples of phenotypic change reported in offspring based on maternal treatments reflect prevention of pathology caused by dietary deficiency, e.g., neural tube defects or adverse drug effects such as those induced by diethylstilbestrol (Walker, et al. 1997 Carcinogenesis 18, 791-793) or alloxan (Spergel, et al. 1975 Metab. Clin. Exp. 24, 1311-1319).

Cooney (1993 Growth Dev. Aging 57, 261-273) proposed that dietary methyl supplements given to adults could affect gene expression and 5MC levels in those same individuals and that the level of gene-specific 5MC in young mammals might affect their adult health and longevity. The present study is the first to reveal that specific methyl supplements in the diets of pregnant mouse dams can affect the expression of a specific gene, agouti, or a basic gene control element, LTR, even in the offspring. Therefore, maternal supplementation had beneficial health effects in adulthood for the offspring by preventing some of the health problems associated with ectopic agouti expression. Maternal supplements also increased DNA methylation in offspring (Example 9).

Without wishing to be bound by any particular mechanism of action, the mechanisms for these effects of methyl supplements on epigenetic phenotype and DNA methylation are believed to be based on changes in methyl metabolism that extend to the embryos. These changes affect DNA MTase activity by increasing the substrate SAM or decreasing the inhibitor SAH in early embryos, and thus increase the level of DNA methylation in early embryos.

There is also an interplay with strain background genome in that MS diet has a clear effect on strain VY but not on strain YS mice. Again, a likely mechanism would be differences in aspects of methyl metabolism between these two strains. Note that these two strains also differ in the proportion of EM in offspring from dams on control diet. Apparently, one or more of the MS supplement components are limiting in the control diet for dams of the VY strain, but not for those of the YS strain.

Both strains respond to 3SZM supplement, which indicates that one or more of the 3SZM supplement components are limiting in the control diet for VY strain mice and in the MS diet for YS strain mice. In addition, the appearance of the "'almost pseudoagouti'" phenotype in both strains on 3SZM diet indicates that one or more of the 3SZM supplement components are limiting with respect to one or more aspects of methyl metabolism in the MS diet for strain VY mice, at least for inducing this phenotype in offspring. The most obvious mechanisms for the effects of 3SZM supplement are on methyl metabolism and/or on zinc availability. Saturation of the DNA MTase with zinc may also affect its activity or specificity and thus affect the methylation level or pattern on DNA.

There may be other less direct or apparent mechanisms for the effects of these supplements on the epigenetics and development of offspring. Choline, directly from the diet or synthesized via methyl metabolism, is known to affect cell membrane fluidity, membrane-bound enzyme activity, and intracellular signal transduction. Likewise, methionine and folates have essential functions in, development including protein and DNA synthesis. Effects on these parameters could be important in embryonic development and epigenetics. Similarly, zinc has numerous biological functions and could act via other mechanisms to affect epigenetics in development. For example, numerous zinc finger proteins besides DNA MTase are important for cellular differentiation in development.

In humans, folic acid supplements are important for preventing some neural tube birth defects. Because present supplementation levels in humans do not prevent all such defects, it is useful to know what supplementation levels are toxic in mammalian development. In this study, surprisingly, we found no evidence of toxicity at high levels of supplementation in mice.

Whereas most mottled yellow $A^{vy}/a$ mice become fat, are hyperinsulinemic, and are more susceptible to tumor formation, pseudoagouti $A^{vy}/a$ mice remain lean, are normoinsulinemic, and have significantly lower lindane-associated liver tumor prevalence. Data from Wolff, et al. (1987, Carcinogenesis 8, 1889-1897) reveal that, between about 17 and 24 months of age, only 24% of pseudoagouti $A^{vy}/a$ (YS×VY) $F_I$ females died compared with 50% of mottled yellow $A^{vy}/a$ and 23% of black a/a female mice; no differences in mortality between the lindane-treated and untreated control mice were observed. Thus, by increasing the proportion of the phenotype with a down-regulated $A^{vy}$ allele, the maternal methyl-supplemented diets direct the differentiation of more $A^{vy}/a$ embryos toward a relatively healthier and longer lived phenotype.

EXAMPLE 7

Use as a Nutritional Supplement

We are the first to show that a maternal nutritional supplement can change an epigenetically regulated process in mammalian offspring. More specifically the supplement changed gene or sequence specific DNA methylation. Additionally, it was shown that these changes were beneficial. This is the first time that any maternal treatment (other than transgenic or transkaryotic manipulation) was able to change DNA methylation in mammalian offspring.

From these results it is clear that there is a use for various combinations of the six methylation-enhancing agents such as were used in the 3SZM diet as a nutritional supplement. It was unexpected that these compounds would have a positive effect on the fetus, when administered to the parent. It was also unexpected that these compounds could be used prenatally at high levels without adverse effects on fetal development. Therefore, the compositions have utility as prenatal supplements for improving the health and longevity of the offspring as well as a number of other uses. Levels necessary for other mammals could be extrapolated from these mouse models by one of skill in the art.

This technology has the following reasonable applications as a nutritional supplement or nutraceutical or pharmaceutical or drug or functional food: Using the nutritional supplement to change the coat color pattern or other cosmetic appearance of mammalian offspring, to change the epigenetically determined phenotype or characteristic of mammalian offspring, to improve the epigenetically determined health or longevity of offspring, to improve the health or longevity of offspring, to change epigenetics of offspring, to mimic genetic strain effects on offspring.

Another application would be using a maternal nutritional supplement or its in vitro equivalent to prepare, treat, design or modify oocytes or zygotes in assisted reproduction procedures. Such treatment of oocytes or zygotes either in vivo or in vitro could be used to achieve some of the same purposes described above.

As an example, the following levels are believed to be of use as part of the diet or along with the diet. Per kg of diet the following levels of supplement:

5 g to 15 g Choline
5 g to 15 g Betaine
5 mg to 15 mg Folic acid 0.5 mg to 1.5 mg Vitamin $B_{12}$
0 to 7.5 g L-Methionine
0 to 150 mg Zinc These levels or higher are reasonable applications of this invention. The low end of each range represents the amounts in MS diet and the higher end of each range represents double the 3SZM diet. For humans consuming about 500 g of food per day these amounts would be:

2.5 g to 15 g Choline
2.5 g to 15 g Betaine
2.5 mg to 15 mg Folic acid
0.25 mg to 1.5 mg Vitamin $B_{12}$
0 to 7.5 g L-Methionine
0 to 150 mg Zinc These are the daily doses and they can be administered in single or multiple administrations. While intake of the above formula or subsets thereof orally, i.e. in the diet (as a solid i.e. food, tablet or powder etc., or as a liquid to drink or mix with food), is the preferred method, other useful methods could include injection, suppositories, transdermal patches etc. This supplement could be used in the absence of food for example at a different time of day than a meal or during a fast where no food was consumed during the day.

EXAMPLE 8

Use as an Inhibitor of Retroviral Expression

We are the first to show that any maternal treatment (other than transgenic or transkaryotic manipulation) can change expression or activity of a retroviral, retrovirus-like, parasitic DNA sequence, LTR, promoter or similar transcription activating sequence which is endogenous in the genome, in mammalian offspring. Or that a maternal nutritional supplement can change expression or activity of a retroviral, retrovirus-like, parasitic DNA sequence, LTR, promoter or similar transcription activating sequence, in mammalian offspring.

Therefore, because expression of IAPs and other retrovirus and retrovirus-like elements (types o f repetitive DNA elements) results in a variety of health problems in mice, humans, and other mammals, it would be of interest to be able to suppress or inhibit the expression of these elements. Mammalian genomes carry thousands of parasitic DNA elements that carry their own genes and pose a hazard to health if activated. These include Endogenous Retroviruses (IAPs and others) and L1 sequences. These sequences carry the means (LTRs and functional equivalents) to activate their own genes and will, in many cases, activate other nearby genes as is the case with the IAP in the $A^{vy}$ allele and the agouti gene it activates. As with the $A^{vy}$ IAP, DNA methylation suppresses the LTRs and other transcription activating sequences of other parasitic sequences and keeps them inactive. However, parasitic sequences can avoid methylation and activate their own and nearby genes causing one or another variety of health problems for humans and other mammals. These same considerations extend to exogenous retroviruses. Some researchers feel that HIV will join human genomes in the germline and become an endogenous retroviral sequence or retroviral-like sequence as IAPs have become in mice.

It is clearly shown in the above experiments and in Example 9, with the mouse model, that methylation of the IAP LTR inhibits retroviral activation of expression. Thus methylation of any IAP gene or any retroviral sequence that is controlled by methylation in an animal would inhibit retrovirus expression from those sequences.

This then is a second use of the nutritional supplement. The supplement would be given as shown in Example 7. Retroviral sequences as defined include the following: a retroviral, retrovirus-like, parasitic DNA sequence, LTR, promoter or similar transcription activating sequence, including DNA sequence motifs included within the retroviral, retrovirus-like, or parasitic DNA sequence or LTR that activate genes and that are suppressed or controlled by DNA methylation or epigenetic factors. The supplement would be used to protect against sequences endogenous in the genome of mammalian offspring or could be used to prepare offspring for use of their organs, tissues or other derived biologics in xenotransplantation into or other use in other species including humans or other animals.

Another application would be using a maternal nutritional supplement or its in vitro equivalent to inhibit retroviral sequences in oocytes or zygotes in assisted reproduction procedures.

EXAMPLE 9

Use as an Animal Model

We are the first to show an animal model in which maternal treatments can be screened for producing epigenetic changes (and specifically DNA methylation) in offspring that can be readily monitored by visual or other unaided sensory evaluation. This can reasonably be expected to produce multigenerational effects. The fact that the changes can be monitored visually is a particularly advantageous aspect of the invention. It provides for an inexpensive, reliable, expedient test that doesn't require undue technical skills to be performed.

An animal model in which maternal treatments can be screened for producing changes in the expression or activity of a retroviral, retrovirus-like, parasitic DNA sequence, LTR, promoter or similar transcription activating sequence, endogenous in the genome, in offspring that can be readily monitored by visual or other unaided sensory evaluation.

The animal model could also be used to screen for effects of maternal treatments which produce epigenetic changes in offspring that can be readily monitored by visual or other unaided sensory evaluation and that can be reasonably expected to produce multigenerational effects.

The animals used in this study are known in the art. However, they have never been used as an animal model for determining if manipulation, particularly manipulation of maternal diet, can alter the phenotype of offspring. The model permits a rapid screen for an intergenerational effect. Because coat color pattern is indicative of future health and longevity in these $A^{vy}/a$ animals and is identifiable in mice once the coat appears at 7 days of age, adult characteristics of this epigenetic phenotype can be predicted at 1 wk of age. Therefore, several generations of animals, categorized by their predicted relative long-term health and longevity, can be produced within about 2 years to determine the multigenerational effects of diet or drugs on relative health and longevity.

The test would be -carried out as follows: using an animal model in which a female mouse homozygous for the recessive non-agouti allele (a/a) is impregnated by a male mouse heterozygous for the dominant viable yellow allele ($A^{vy}/a$). A test treatment is administered to the pregnant female and the phenotype of the offspring is measured. The phenotype of the offspring is determined by visual examination of their coat color pattern. In addition or alternatively the level of 5MC on the IAP LTR of the $A^{vy}$ allele can be measured.

The technique for DNA methylation analysis is included below, however, any experimental technique for analysis of DNA methylation could be used.

DNA Methylation Analysis

DNA methylation, the enzymatic addition of a methyl group (—CH$_3$) to the 5-position of the cytosine ring in the DNA polymer, is a common DNA modification mechanism used to control DNA sequence expression and activity. Assays are described here to show that DNA methylation differences exist in the IAP LTR proximal to the agouti gene between the most highly mottled phenotypes and the least mottled phenotypes of A$^{vy}$/a mice.

The methods used are widely recognized and are outlined below.

DNA Isolation

Any of several widely available means of isolating DNA suitable for restriction digestion and polymerase chain reaction (PCR) will work here. A solution of guanidinium thiocyanate (GT, Chomczynski et al. 1997, BioTechniques 22, 550-553), which contains chaotropic agents that disrupt tissue, was used in the following experiments. First, the tissue (liver or kidney) was homogenized in GT. Second, the homogenate was centrifuged for 19,000×g at 4° C. for 20 minutes. This sedimented insoluble components of the sample. The supernatant was transferred to another tube. Up to one volume of ethanol was added to precipitate DNA from the supernatant. Ethanol is added and tubes are inverted so that the DNA becomes visible as a cloudy precipitate, which is transferred to another tube. Fourth, the DNA is washed several times with ethanol to remove contaminants from the sample. In the final step, the DNA, now in the form of a pellet, is dissolved and stored in a solution (pH 7.4) composed of 10 mM Tris-HCl, 0.1 mM DisodiumEDTA (TE).

Genomic DNA Isolation Using GT

1. Homogenization of tissue.

Using a Teflon pestle in a 1.5 ml microcentrofuge tube (MCT), 25-50 mg tissue (liver or kidney or other) was homogenized in 200 ul of GT. Once homogenized, 800 ul more GT was added and pipetted gently to moderately to mix and slightly reduce the size of DNA (to make the solution less viscous). Samples were stored for 5-10 min. at room temperature.

2. Centrifugation.

Homogenate was sedimented for 20 minutes at 19,000×g at 4° C. in a microcentrifuge. A pipette was used to recover homogenate supernatant leaving insoluble material behind in the pellet.

3. DNA Precipitation

DNA was precipitated from homogenate supernatant by addition of 0.5 ml 100% ethanol. Samples were mixed vigorously by hand by inverting assay tubes and samples were stored at room temperature for 1-3 min. DNA appeared as cloudy precipitate. DNA was pelleted for 2 minutes at 1000×g at 4° C. Supernatant was removed by pipetting.

4. DNA Wash

DNA precipitate was washed with 0.25 ml of 70% GT:30% EtOH and spun as before. Supernatant was removed by pipetting. DNA precipitate was washed twice with 0.8-1.0 ml of 95% ethanol. During each wash, the DNA was suspended in ethanol by inverting the tubes several times. DNA was sedimented by pelleting at 1000×g at 4° C. and ethanol removed by pipetting.

5. DNA Solubilization

Remaining alcohol was removed from the bottom of the tube using a pipette. DNA pellets were dried under vacuum (in a vacuum centrifuge) and dissolved in TE and left overnight at 4° C. To break up DNA clumps the solution was pipetted. DNA solution was sedimented for 15 minutes at 19,000×g at 4° C. to pellet any particulates. Supernatants were transferred to fresh tubes and 100 ul of TE was added to each pellet which was mixed and sedimented for 15 minutes at 19,000×g at 4° C. These second supernatants were recovered to the corresponding tubes containing the first supernatants.

6. DNA Quantitation

DNAs were mixed well and a small aliquot of each was taken and diluted 50 fold with TE. The ultraviolet absorbance of this was then measured at 260 nm and 320 nm versus a blank of TE. The concentration of DNA was calculated from the absorbance at 260 nm minus the absorbance at 320 nm by conventional means, e.g. (A260-A320)×50 ug/ml/1.0A×50 (dilution). Thus, a sample with an A260 of 0.405 and an A320 of 0.005 had an original concentration before dilution of 0.400×50ug/ml×50=1000 ug/ml or 1 mg/ml. Other means to accurately determine DNA concentration would also work here.

7. DNA Restriction Digestion and Polymerase Chain Reaction

Figure 2:
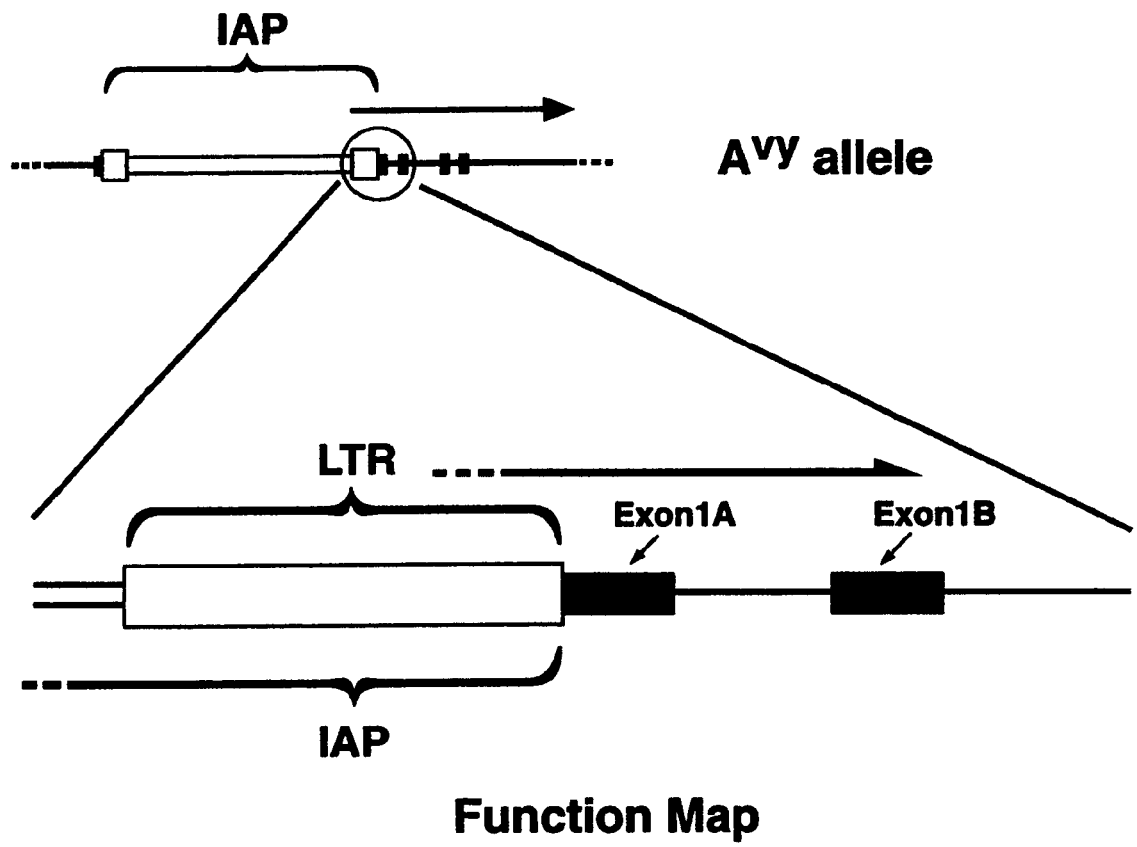
FIG. 2. A schematic of the DNA and restriction sites used. In the "Function Map" of the $A^{vy}$ allele, an IAP is shown inserted in Exon 1A of the agouti gene. Transcription initiates from the proximal IAP LTR (Duhl et al. 1994 Nature Genetics 8, 59-65). In the "Restriction Site and Primer map" some restriction sites containing CpGs are shown within the LTR. PCR primers are shown on either side of the LTR. Both HaeII (H) and HinPlI (P) are methyl sensitive restriction enzymes, i.e. they will not cut DNA if the sequence is PuGMCGCPy or GMCGC, respectively. (Note that all HaeII sites are also HinP1I sites but not conversely.) The arrangement shown is approximate and may be refined and changed with further study. Expression in this and other arrangements of IAPs and their LTRs are affected by DNA methylation. This and other arrangements of IAPs and their LTRs can affect the expression of adjacent genes.
Figure 2:
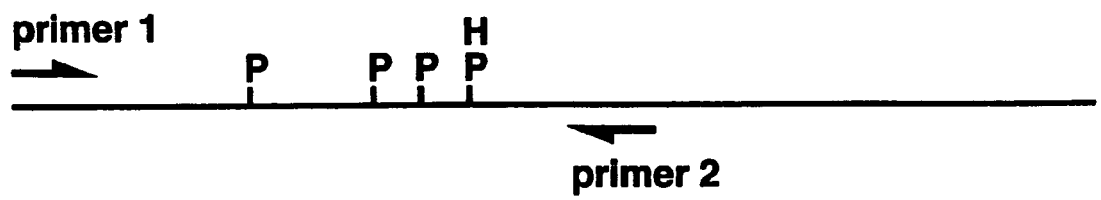

A set of DNA primers for PCR was designed using one of the primers described by Duhl et al. (1994) Nature Genetics 8, p59-65, namely "GAGTTTAGCACATACCTTCT" (referred to as AVYCC856) (SEQ ID No. 2) and another primer designed by Craig Anthony Cooney, 1st inventor (unpublished) based on the sequence of Algate & McCubrey (1993) Oncogene 8, p1221-1232, namely "AATTTTCAGC-CCTATCTTAA" (referred to as AVYCC6) (SEQ ID No. 1). The primers AVYCC6 and AVY856 are designed to span across the A$^{vy}$ IAP LTR. Thus the PCR product of these two primers includes the entire LTR and flanking sequence on each side (FIG. 2). On the AVYCC6 side the flanking sequence is the IAP sequence and on the AVYCC856 side the flanking sequence is agouti gene exon 1A. The IAP LTR is the sequence driving the overexpression of the agouti gene in yellow phenotype A$^{vy}$/a mice. The likely linkage of the sequences AVYCC6 and AVYCC856 was made by Craig Anthony Cooney, 1st inventor (unpublished) by extrapolating from the extensive sequence alignment between the A$^{vy}$ allele IAP LTR sequence and the IL3 IAP LTR and IAP gag gene sequence. The contiguous sequence between the LTR sequence of and agouti gene Exon 1A is available in GEN-BANK (locus MUSAGOUA, accession number L76476, the agouti gene sequence used here for PCR is set out as SEQ ID No. 3). PCR amplification from A$^{vy}$/a mice produces an 870 bp product characteristic of the A$^{vy}$ allele. DNA from a/a mice does not give this 870 bp product. One HaeII site and four HinP1I sites are found in the IAP LTR (FIG. 2). The primers used for PCR are shown as SEQ ID No. 1 and 2, primer 1 is AVYCC6 and primer 2 is AVYCC856. Both HaeII and HinP1I are methyl sensitive restriction enzymes (Note that all HaeII sites are also HinP1I sites but not conversely). This HaeII site is conserved in IAP LTRs and others (Lueders 1995 Electrophoresis 16, 179-185) have used this conserved HaeII site in IAP LTRs to measure DNA methylation (by different methods and in different IAPs than that in A$^{vy}$).

In a preferred way to demonstrate methylation, each PCR reaction contains genomic DNA digested with restriction enzyme or an undigested control DNA. All heating steps are best done in a conventional PCR tube under a layer of wax designed for the purpose and known in the art. This DNA is heated in a small volume of water (e.g. 15 ul) to 95° C. for 20 min. to inactivate the restriction enzyme. After cooling and wax solidification a conventional, widely used, "hot start" procedure is best used where buffer, dNTPs, MgCl$_2$ and primers are added and heated to 80° C. for 5 minutes. After cooling and wax solidification additional buffer and Taq polymerase are added (final MgCl$_2$ concentration is 1.25 mM) and the following thermocycling procedure is followed: 94° C. for 60s, then 30 cycles of: (94° C. for 30s, 56° C. for 30s, 69° C. for 30s); lastly one cycle of 72° C. for 600s; Cool to 4° C. indefinitely. Products are assayed by agarose gel electrophoresis.

Although the above is a preferred method, several variations (in the buffer type, dNTP concentrations, $MgCl_2$ concentration, primer concentrations, thermocycling program) of this PCR method will also produce the 870 bp fragment. Similarly a wide variety of other techniques (including, but not limited to, bisulfite sequencing, Maxam-Gilbert sequencing with ligation mediated PCR, restriction digestion with Southern blotting) for measuring DNA methylation in mammals could be used.

Thus this PCR primer set and these enzymes can be used to determine if DNA of $A^{vy}$/a mice has this LTR methylated by isolating DNA, cutting it with either of these enzymes, heat inactivating the enzyme by heating to 95° C. for 20 minutes, and PCR amplifying the resulting DNA. A control is run where half the sample is set aside before restriction digestion and heated and otherwise treated identically except that water is added in place of restriction enzyme. In this control no diminution of PCR amplification will take place as a result of unmethylated sites in the DNA. In the restricted samples diminution of PCR amplification takes place as a result of cleavage of the unmethylated sites in the $A^{vy}$ sequence in the IAP LTR. Cleavage of these unmethylated sites results in fewer intact copies of the sequence to be amplified and a lower amount of PCR product. The PCR products from the control and restricted DNA samples are run side by side on an agarose gel.

8. Agarose Gel Electrophoresis

PCR products are analyzed by agarose gel electrophoresis. An 0.8% to 1.0% agarose gel was prepared for this purpose using 0.5×Tris-Borate-EDTA buffer. 10 ul of each PCR product was mixed with 3 ul of a standard tracking dye mixture and loaded in a separate well of the gel. A ladder of DNA size markers (a 1 kb ladder) is added as a size reference. The gel was run for about 2 hrs. at 15 mA and 50 V. The gel was then stained with ethidium bromide for 30 minutes, destained twice in water for 20 minutes each time and viewed under UV fluorescent light. A digital or photographic image was made of the gel to produce a permanent record of the pattern and intensity of the DNA bands.

In each case studied, the restriction digested DNA from pseudoagouti and 'almost pseudoagouti' mice (9 out of 9 mice) gave a strong signal similar in intensity to the control (e.g. 60 to 100% of control level) and indicating a high to full level of methylation on the HaeII site and/or all four of the HinP1I sites, in the LTR. In each case studied the restriction digested DNA from clear yellow and slightly mottled, yellow mice (5 out of 5 mice) gave a weak or no signal compared to the control (e.g. 0 to 10% of control level) indicating a low or zero level of methylation on the HaeII site and/or at least one of the four HinP1I sites in the LTR. DNAs of both YS and VY mice were used showing that DNA methylation differences between phenotypes exist for both strains.

Likewise DNA from 16 day fetuses (normal gestation is 21 days) was used to show which fetuses were $A^{vy}$/a (because they produced the 870 bp product in PCR) and that in some of these fetuses the $A^{vy}$ IAP LTR was heavily methylated at its HaeII site. Quantification of PCR product amounts can be done by analysis of the digitized gel image by any of a number of standard techniques. Several DNA samples can be run on the same gel so that they can be most directly compared. Samples can include those with a known amount of $A^{vy}$ sequence so as to determine the efficiency or linearity of the PCR reaction and, if necessary, to form a calibration curve for quantifying the amount of $A^{vy}$ sequence in a particular sample.

The animal model is useful for testing the effects of maternal treatments on epigenetic regulation of phenotype of offspring, particularly where phenotypes are known or suspected to be regulated by DNA methylation and more particularly where phenotypes are known or suspected to be regulated by DNA methylation of an IAP sequence, an LTR sequence or subsets thereof. This model is useful for testing for effects on embryonic development including but not limited to genomic imprinting. Also an animal model in which epigenetic inheritance has been demonstrated and thus is useful for the study of multigenerational effects due to epigenetic and/or gene specific mechanisms.

Although the effects on maternal epigenetic inheritance were significant in the experiments described, they apparently did not interfere with normal biological development or with the high degrees of methylation, demethylation, and other epigenetic changes required in the development and growth of embryos. These moderate effects and the partial expression and penetrance of $A^{vy}$ make this experimental system with visual markers well suited for study of the effects of diet and drugs on epigenetic modulation of gene expression. In contrast, systems in which epigenetic control is complete do not provide the sensitivity to monitor subtle to moderate changes in gene expression.

The coat color markers reflecting $A^{vy}$ expression in development are important because, even with PCR techniques, evaluation of mosaic phenotypes in animal populations is difficult; however, coat color markers such as those induced by $A^{vy}$ make identification easy. For these reasons as well as the maternal epigenetic inheritance of phenotype, this $A^{vy}$/a experimental system should be useful for identifying factors that modulate epigenetic mechanisms, e.g., DNA methylation in developing embryos and over multiple generations.

What is claimed is:

1. A method for screening compounds that affect mouse agouti coat color prevalence in progeny heterozygous for agouti alleles, comprising:

administering a treatment consisting of one or more candidate compounds to a homozygous a/a female;

crossing the a/a female with an heterozygous $A^{vy}$/a male;

determining the prevalence of agouti coat color phenotypes in $A^{vy}$/a progeny; and comparing the prevalence of agouti coat color phenotypes in $A^{vy}$/a progeny to similar prevalences found in $A^{vy}$/a progeny of genotypically identical matings that have had no such treatment, wherein an increased prevalence of agouti coat color is indicative of a compound effective in increasing the agouti coat color with known associated decreases in the prevalence of associated cancers, obesity and diabetes, and increased longevity, in such progeny, and wherein a decreased prevalence of agouti coat color is indicative of a compound effective in decreasing the agouti coat color with known associated increases in the prevalence of associated cancers, obesity and diabetes, and decreased longevity, in such progeny.

2. The method according to claim 1, wherein the determining the prevalence of agouti coat color phenotypes in $A^{vy}$/a progeny comprises measuring the percentage of agouti coat color on the $A^{vy}$/a progeny.

3. The method according to claim 1, wherein the determining the prevalence of agouti coat color phenotypes in $A^{vy}$/a progeny comprises assigning the progeny mice to phenotypic categories based on the percentage of agouti coat color.

4. The method according to claim 1, wherein the determining the prevalence of agouti coat color phenotypes in $A^{vy}$/a progeny comprises assigning the progeny mice to categories of high eumelanic mottling and low eumelanic mottling.

5. The method according to claim 1, wherein the agouti coat color phenotypes in $A^{vy}$/a progeny comprises agouti on a yellow background.

6. The method according to claim 1, wherein the agouti coat color phenotypes in $A^{vy}$/a progeny comprises yellow on an agouti background.

7. The method according to claim 1, wherein the agouti coat color phenotypes in $A^{vy}$/a progeny comprises the almost pseudoagouti phenotype.

8. The method according to claim 1, wherein the one or more of said candidate compounds is selected from the group consisting of betaine, choline, folic acid, methionine, vitamin B12, and zinc.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: PCR primer AVYCC6 designed to span the IAP LTR

<400> SEQUENCE: 1

```
aattttcagc cctatcttaa                                                    20

<210> SEQ ID NO 2
<211> LENGTH: 20
<212> TYPE: DNA
<213> ORGANISM: Artificial Sequence
<220> FEATURE:
<223> OTHER INFORMATION: PCR primer AVYCC856 complementary to
      agaaggtatgtgctaaactc and designed to span the IAP
      LTR

<400> SEQUENCE: 2
gagtttagca cataccttct                                                    20

<210> SEQ ID NO 3
<211> LENGTH: 922
<212> TYPE: DNA
<213> ORGANISM: Mus musculus intracisternal A particle (IAP)

<400> SEQUENCE: 3
tctagaattt tcagccctat cttaagcact atataacatg tgaaaaggaa caaaagggct         60
tctaacacta gaaaaaattt aaggccaaac ataacttgta aagccatttt ccactttact        120
tctgatagac tgtcttgaat ttccttagaa agttcaagat cagacttacc tcgttcccca        180
gctgaaaagt tctgaattca tacagttgaa tccttcttaa cagtctgctt tacgggaacc        240
tttatcaccg tcgttcccca gctgatgagt tctgaattcg gcagttgaat ccttctcaac        300
agtctgtgtt acgggaacct tataaccttg attcgcagtt ctggttctgg aatgaggtat        360
ccctcctgcg ccagtccgga gttttttctc gtcccggatt ttctcgtccc ggaattccgg        420
gcaccaattg ttattcgacg gctttccttc accgaccggc caggaagaac accacaagac        480
cagaatcttc tgcgacaaag ctttattctt acatcttcag gaaaagagag caagaagcaa        540
gagagagaga aaaacgaaac cccttctatt ttaaagagaa caaccattgc ctagggcgca        600
tcactccctg attgctgcag cccatggccg agctgacgtt cacgggaaaa acaggtacaa        660
gtggtcgtaa ataccttgg ctcatgcgca gttatttgtt taccaactta gaacacagga         720
tgtcagcgcc atcttgtgac ggcgaatgtg ggggcggctt cccacaccat ttcccaccag        780
tccaagtcct tgagcctctg cagcctcaga agagggagtc atcagctgaa acctccagga        840
accaccgggg gtcccagaag gtatgtgcta aactccatcc agatgttgtg tttcgttttg        900
ttctttttct tcttttttcc tc                                                 922
```